United States Patent
Netzhammer

(10) Patent No.: US 7,810,528 B2
(45) Date of Patent: Oct. 12, 2010

(54) TRANSPORT CONTAINER FOR STERILE PRODUCTS

(75) Inventor: Erich Friedrich Netzhammer, Muttenz (CH)

(73) Assignee: Eric Netzhammer, Bottmingen (CH)

(*) Notice: Subject to any disclaimer, the term of this patent is extended or adjusted under 35 U.S.C. 154(b) by 0 days.

(21) Appl. No.: 12/010,258

(22) Filed: Jan. 23, 2008

(65) Prior Publication Data

US 2008/0149218 A1  Jun. 26, 2008

Related U.S. Application Data

(63) Continuation of application No. 11/046,858, filed on Feb. 1, 2005, now abandoned.

(30) Foreign Application Priority Data

May 4, 2004  (CH) .................................... 0788/04

(51) Int. Cl.
  *B65B 1/04* (2006.01)
(52) U.S. Cl. .................. 141/327; 141/325; 141/383
(58) Field of Classification Search ................ 141/69, 141/87, 98, 231, 325, 327, 383
  See application file for complete search history.

(56) References Cited

U.S. PATENT DOCUMENTS

| 5,029,624 A | 7/1991 | McCunn et al. |
| 5,263,521 A | 11/1993 | Brossard et al. |
| 5,289,858 A | 3/1994 | Grabenkort |
| 5,490,546 A | 2/1996 | Lhoest |
| 5,715,646 A | 2/1998 | Smekens |
| 5,946,217 A | 8/1999 | Lhoest |
| 6,357,488 B1 | 3/2002 | Brossard |

FOREIGN PATENT DOCUMENTS

| EP | 1 253 095 A1 | 10/2002 |
| WO | WO-98/43902 | 10/1998 |

*Primary Examiner*—Timothy L Maust
(74) *Attorney, Agent, or Firm*—Fitch, Even, Tabin & Flannery; Norman N. Kunitz

(57) ABSTRACT

The transport container serves for transporting sterile products, for example caps or stoppers for pharmaceutical purposes, from a sterilization facility to a downstream facility, for example a filling plant. It has two connecting devices which are arranged opposite one another and one of which is equipped with a rapid transfer port for docking the transport container with the downstream facility and the other is a filling device. The rapid transfer port is equipped with a cover which is provided with an opening device for opening the port cover. In addition, the rapid transfer port is preferably provided with a medium outlet through which cleaning and sterilization media can be discharged when the port cover is opened.

2 Claims, 2 Drawing Sheets

TRANSPORT CONTAINER FOR STERILE PRODUCTS

CROSS-REFERENCE TO RELATED APPLICATION

This is a continuation of application Ser. No. 11/046,858, filed Feb. 1, 2005, and claims the benefit of priority under 35 U.S.C. §119 of Swiss Application 2004 0788/04, filed May 4, 2004, the entire disclosures of which are hereby incorporated by reference.

BACKGROUND OF THE INVENTION

1. Field of the Invention

The present invention relates to a transport container for transporting sterile products from a sterilization facility to a downstream facility for the intended use of the products, and the sterile docking with the downstream facility, comprising two connecting devices which are arranged opposite one another and one of which is equipped with a rapid transfer port for docking the transport container with the downstream facility and the other is a filling apparatus.

The products are, for example, small parts, such as caps or stoppers for pharmaceutical uses. The downstream facility is, for example, a filling plant for pharmaceutical products. Thus, during docking of the transport container, the purity and the sterility of the products and of the parts with which the products come into contact must be ensured.

2. Description of the Prior Art

For the cleaning and sterilization of caps and stoppers in the pharmaceutical industry, various processes for treatment and various methods for docking with the next production stage are known.

A customary process comprises cleaning and sterilizing the closure parts in a treatment facility and, after the treatment, filling them into a transport and storage container. The filled container is then undocked from the treatment facility. The container is usually subjected to pressure so that contamination of the closure parts from the atmosphere is ruled out.

If required, the containers are moved to the next process step, for example a filling machine. Usually, the further processing takes place in a clean room or in an isolator. A docking process takes place there. What is decisive is that, during the further processing, the closure parts never come into contact with an unclean environment, i.e. an environment which is not clean and not sterile. All docking processes must therefore be effected under sterile conditions so that no contamination of the closure parts with the atmosphere can take place. In this case, the container has only the function of a storage and transport container. No treatment of the content takes place therein.

After the treated closure parts have been introduced into the transport and storage container, a rapid transfer port known per se is manually fastened to the filling opening. The attached adapter must then be cleaned and sterilized with known agents. After this process, the storage container is ready for docking at the next process stage. This method has the disadvantage that firstly a manual operation is necessary with the attachment of the port and that secondly the cleaning and sterilization of the port cannot be carried out simultaneously with the process.

Another known process comprises treating the closure parts in a multifunctional container and then storing and transporting them in this container.

In order to achieve good cleaning and sterilization results, large amounts of cleaning agents, air for drying and steam for sterilization are required. These media must as a rule flow from bottom to top through the material. The multifunctional container therefore requires an upper and a lower process connection so that the required media can flow through the material. After the treatment, the multifunctional container is undocked from the treatment facility. The closure parts are transported and stored in the multifunctional container under superatmospheric pressure.

For the further use, the procedure is as in the case of the first process. In order to permit both the cleaning and sterilization treatment and the docking in the subsequent process stage, the multifunctional container is equipped at the top with a Y-connection. One connection serves for carrying out the process and the other is equipped with a rapid transfer port. With this facility, it is possible to mount the rapid transfer port firmly on the container. Manual attachment of the port is dispensed with. The port is equipped with a cover. A disadvantage of this method is that the media (cleaning agent, steam) cannot flow through the port, which is bacteriologically disadvantageous, since it is good practice for the medium to flow completely through the parts in contact with products during the cleaning and during the sterilization.

An additional disadvantage is the fact that the port seal is not cleaned and not sterilized, since the port cover is not removed during the cleaning and sterilization process. In addition, the construction of the Y-connection is very complicated. However, this construction is necessary in this process since the process connections cannot be used as port connections.

During the docking process, the material falls downward and mechanical means (in this case by means of a screen) have to be used to prevent the material from falling in the direction of the process connection.

U.S. Pat. No. 5,490,546 discloses a transport container having an outlet opening arranged on its bottom and a filling opening for sterile or hazardous products, arranged opposite on the top. Both openings are provided with caps, which are opened by means of actuating devices present there during docking with a pipe, another container or the like. This transport container, too, has the above-mentioned disadvantage with regard to the possibility of incomplete cleaning and sterilization.

SUMMARY OF THE INVENTION

In view of the disadvantages of the systems known in the prior art, it is the object of the invention to find a solution in which these disadvantages are not present.

According to the invention, this object is achieved by a transport container for transporting sterile products from a sterilization facility to a downstream facility for the intended use of the products, and the sterile docking with the downstream facility, comprising two connecting devices which are arranged opposite one another and one of which is equipped with a rapid transfer port for docking the transport container with the downstream facility and the other is a filling apparatus, wherein the rapid transfer port is equipped with a cover which is provided with an opening device for opening the port cover.

BRIEF DESCRIPTION OF THE DRAWINGS

Below, an embodiment of the invention is described with reference to the attached drawings, wherein.

DETAILED DESCRIPTION OF THE INVENTION

Figure 1:
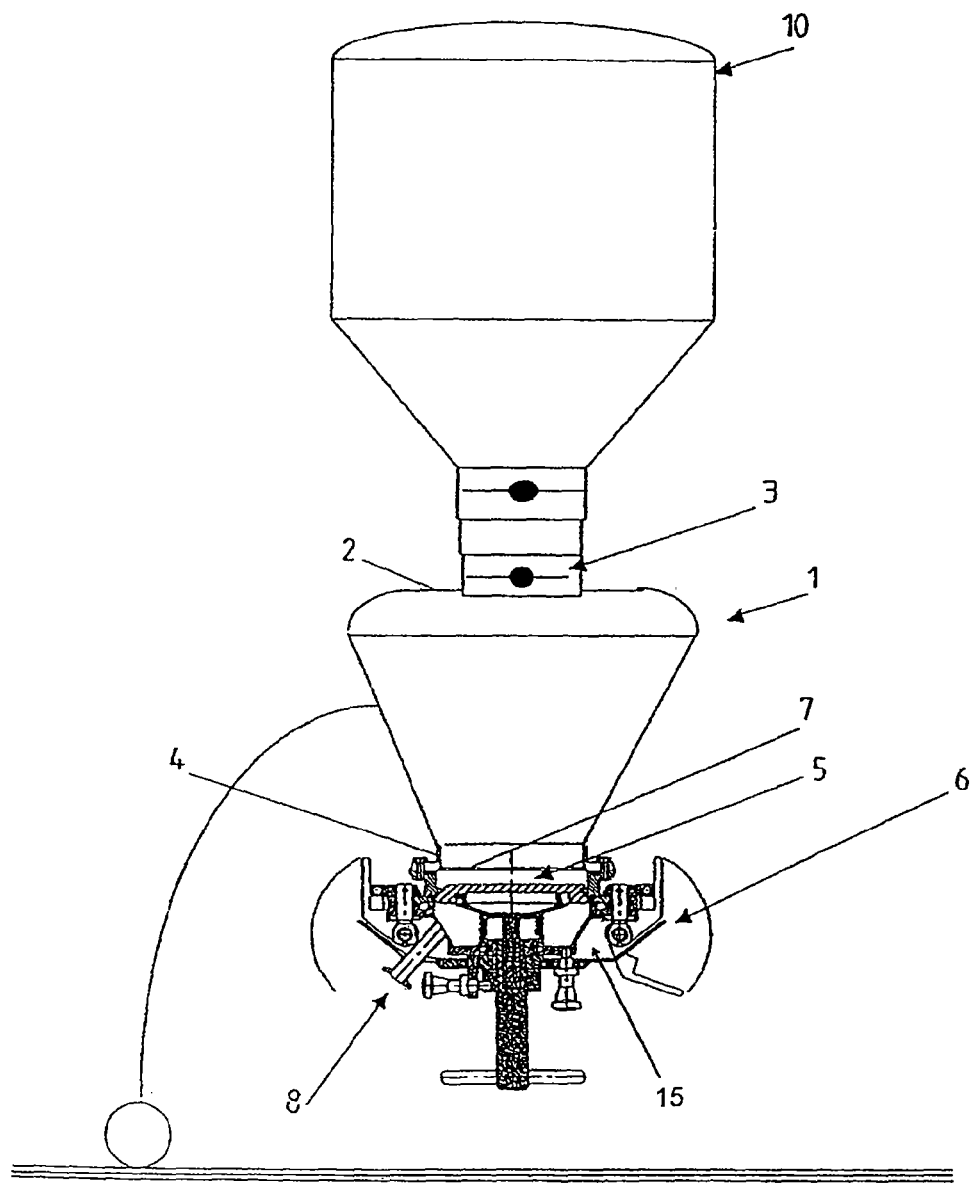
FIG. 1 shows a schematic diagram of a transport container for sterile closure parts.

The transport container 1 shown in the Figure and intended for sterile closure parts, such as caps, stoppers, etc., has a conical shape customary for such containers and, during all process steps, remains in the downward-tapering position shown. On its broad top 2, the container 1 has a filling opening 3 with a filling device through which the sterile closure parts are discharged from a treatment container into the transport container 1.

Before the closure parts are transferred to the transport container, the transport container must be cleaned and sterilized. The transport container is therefore equipped with a medium inlet. Cleaning agent for the cleaning and steam for sterilization can be introduced through this into the transport container.

At its bottom 4, the transport container 1 is provided with a rapid transfer port 5. The rapid transfer port is equipped with an additional cover 6. Such rapid transfer ports provided with a cover are commercially available, for example, under the brand name "La Calhène". The cover 6 makes it possible to clean the port and to sterilize it under pressure. In addition, the media which were required for the cleaning and sterilization of the transport container are discharged through a medium outlet 8 in the cover.

The cover 6 is additionally equipped with a device 15 which makes it possible to open the port cover 7. Both the opening and the closing of the port cover 7 can be effected automatically by means of a suitable drive or manually. This facility thus ensures, in a manner which is satisfactory bacteriologically and in terms of sterilization technology, cleaning and sterilization of all parts which come into contact with the closure parts. All parts coming into contact with the products are cleaned throughout and sterilized throughout. After the cleaning and after the sterilization and the subsequent drying, the port cover is closed again. The inner part of the transport container is thus satisfactorily clean and sterile.

Figure 2:
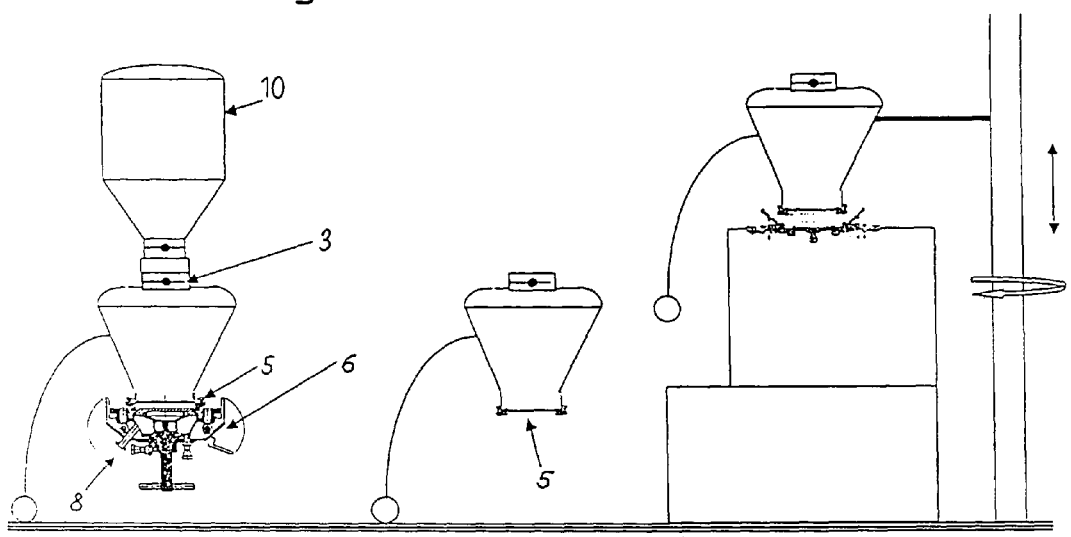
FIG. 2 shows the transport container in three successive process steps.

As shown in FIG. 2, the transport container 1 is connected by its filling opening to a treatment container 10 in a first process step in order to transfer the closure parts cleaned and sterilized in the latter. Thereafter, the closure parts can be stored in the transport container until required for further use in a third step. For this purpose, the transport container is docked by means of the rapid transfer port 5 with a corresponding downstream facility, for example a filling plant.

What is claimed is:

1. A transport container for transporting sterile products from a sterilization facility to a downstream facility for the intended use of the products, and sterile docking with the downstream facility, comprising two connecting devices which are arranged opposite one another and one of which is equipped with a rapid transfer port for docking the transport container with the downstream facility and the other is a filling apparatus, wherein the rapid transfer port, in addition to a port cover for sealing the port, is equipped with an additional cover for covering the port, said additional cover comprising an opening device for opening the port cover when the additional cover is closed and having a separate medium outlet through which cleaning and sterilization media can be discharged from the container when the port cover is opened.

2. The transport container as claimed in claim 1, wherein the transport container has a substantially conical shape with a downward taper, and the rapid transfer port is disposed in a bottom wall of the container.

* * * * *